United States Patent [19]
Pullen

[11] Patent Number: 5,477,861
[45] Date of Patent: Dec. 26, 1995

[54] RESPIRATORY TEST CIRCUITS AND METHODS

[75] Inventor: Paul V. Pullen, Baltimore, Md.

[73] Assignee: The United States of America as represented by the Secretary of the Army, Washington, D.C.

[21] Appl. No.: 180,491

[22] Filed: Jan. 7, 1994

[51] Int. Cl.$^6$ .................................................. A61B 5/08
[52] U.S. Cl. ........................................ 128/716; 128/204.21
[58] Field of Search ..................................... 128/716, 719, 128/724, 725, 204.21–204.23, 204.26

[56] References Cited

U.S. PATENT DOCUMENTS

| | | | |
|---|---|---|---|
| 3,759,249 | 9/1973 | Fletcher et al. | 128/719 |
| 4,681,099 | 7/1987 | Sato et al. | 128/204.23 |
| 5,048,515 | 9/1991 | Sanso | 128/204.26 |
| 5,143,078 | 9/1992 | Mather et al. | 128/716 |

*Primary Examiner*—Angela D. Sykes
*Assistant Examiner*—Samuel Gilbert
*Attorney, Agent, or Firm*—Edward Goldberg; Michael C. Sachs; Edward L. Stolarun

[57] ABSTRACT

A respiration test method for providing accurate test signals which may be used to measure the duration of a subject's inhalation and exhalation periods, and electronic timing circuits for performing such methods. The circuit includes a clock and two flow detectors. One flow detector senses inhalation while the other senses exhalation of a subject. A logic circuit selectively transmits clock pulses from the clock to an inspiratory clock output and an expiratory clock output. The flow detectors generate two-state inhalation and exhalation signals that are at a first state during the duration of the respective inhalation and exhalation periods plus a small timing-out period. The logic circuit, which is connected to clock and the flow detectors, transmits the clock pulses from the clock to the inspiratory clock output when the inhalation signal is at the first state, and to the expiratory clock output when the exhalation signal is at the first state. The logic circuit also includes an overlap detector that generates an overlap pulse when the inhalation signal and the exhalation signals are simultaneously in the first state, and a gate that selectively blocks the transmission of the clock pulses to said inspiratory and expiratory clock outputs in responsive to the overlap pulse.

20 Claims, 2 Drawing Sheets

5,477,861

RESPIRATORY TEST CIRCUITS AND METHODS

The invention described herein may be manufactured, used and licensed by or for the Government for governmental purposes without the payment to me of any royalties thereon.

BACKGROUND OF THE INVENTION

1. Field of the Invention

This invention relates to the field of measuring and testing respiration characteristics of a subject. More particularly, the invention relates to respiration test methods for providing accurate test signals which may be used to measure the duration of a subject's inhalation and exhalation periods, and electronic timing circuits for performing such methods.

2. Description of the Prior Art

Military, law-enforcement, construction, and other personnel often wear respiratory equipment while doing a variety of duties ranging from deploying chemical agents to removing toxic waste to exploring underwater regions. One critical problem confronting designers of such respiratory equipment has been finding ways to increase equipment effectiveness especially during periods when a wearer is doing a strenuous task. Designers have long known that equipment effectiveness can be significantly increased by reducing its physiological burden on the wearer. However, an accurate measurement of the full physiological burden of wearing most respiratory equipment during high-stress periods is often difficult to obtain.

When testing respirators to evaluate their physiological burden on a subject, it has been the general practice to use a flow transducer to measure the volume of expired air and the breathing rate (breaths per minute) of the subject. Designers of respiratory test equipment have recently come to recognize the need to also accurately and reliably measure the actual duration of each of the subject's inhalation and exhalation periods. Most prior art flow measuring systems employed for making such duration measurements have performed satisfactorily when the subject being tested is physically inactive. However, when the subject is active, many prior art systems do not accurately and reliably measure the actual duration of each of the subject's inhalation and exhalation periods.

More specifically, conventional flow transducers used to test respirators typically have a pair of flow meters. One flow meter usually mounts on the inspiratory side of the respirator while the other mounts on the expiratory side. This allows simultaneous recording of the volume flows for both inhalation and exhalation. A commercially available flow meter system that has been successfully used for making such flow measurements is the KL Engineering Kozak Turbine Compensator KTC-3-D. However, this and similar systems have not proved entirely satisfactory for measuring breath duration of an active subject for the reason that synchronization and timing of the inspiratory and expiratory flow transducers are not sufficiently accurate.

SUMMARY OF THE INVENTION

The present invention is directed to a respiration test method for providing accurate test signals which may be used to measure the duration of a subject's inhalation and exhalation periods, and electronic timing circuits for performing such methods. The circuit includes a clock and two flow detectors. One flow detector senses inhalation while the other senses exhalation of a subject. A logic circuit selectively transmits clock pulses from the clock to an inspiratory clock output and an expiratory clock output. The flow detectors generate two-state inhalation and exhalation signals that are at a first state during the duration of the respective inhalation and exhalation periods plus a small timing-out period. The logic circuit, which is connected to clock and the flow detectors, transmits the clock pulses from the clock to the inspiratory clock output when the inhalation signal is at the first state, and to the expiratory clock output when the exhalation signal is at the first state. The logic circuit also includes an overlap detector that generates an overlap pulse when the inhalation signal and the exhalation signals are simultaneously in the first state, and a gate that selectively blocks the transmission of the clock pulses to said inspiratory and expiratory clock outputs in responsive to the overlap pulse.

More specifically, the present invention contemplates a unique respiratory timing circuit and method for use in measuring a subject's inhalation and exhalation durations besides measuring the volume of expired air and the breathing rate (breaths per minute). Generally, the invention includes a respiratory test circuit having a clock for providing clock pulses, an inhalation flow detector for detecting the presence of an inspiratory flow and an exhalation flow detector for detecting the presence of an expiratory flow. The inhalation flow detector provides a two-state inhalation signal having first and second inhalation states. The inhalation signal is at the first inhalation state during the duration of the inspiratory flow plus a timing-out period, and is at the second inhalation state at all other times. The exhalation detector provides a two-state exhalation signal having first and second exhalation states. The exhalation signal is at the first exhalation state during the duration of the expiratory flow plus a timing-out period, and is at the second exhalation state at all other times. A logic circuit has an inspiratory clock output and an expiratory clock output. The logic circuit is connected to the clock and the inhalation and exhalation flow detectors for transmitting the clock pulses from the clock to the inspiratory clock output when the inhalation signal is at the first inhalation state and to the expiratory clock output when the exhalation signal is at the first exhalation state. The logic circuit also includes overlap detectors for generating an overlap pulse when the inhalation signal is at the first inhalation state and the exhalation signal simultaneously is at the first exhalation state. A gate circuit is responsive to the overlap pulse for selectively blocking the transmission of the clock pulses to the inspiratory and expiratory clock outputs.

The exact nature of this invention and other objects and advantages will be readily apparent from consideration of the following specification relating to the annexed drawing.

DETAILED DESCRIPTION OF THE PREFERRED EMBODIMENT

Figure 1:
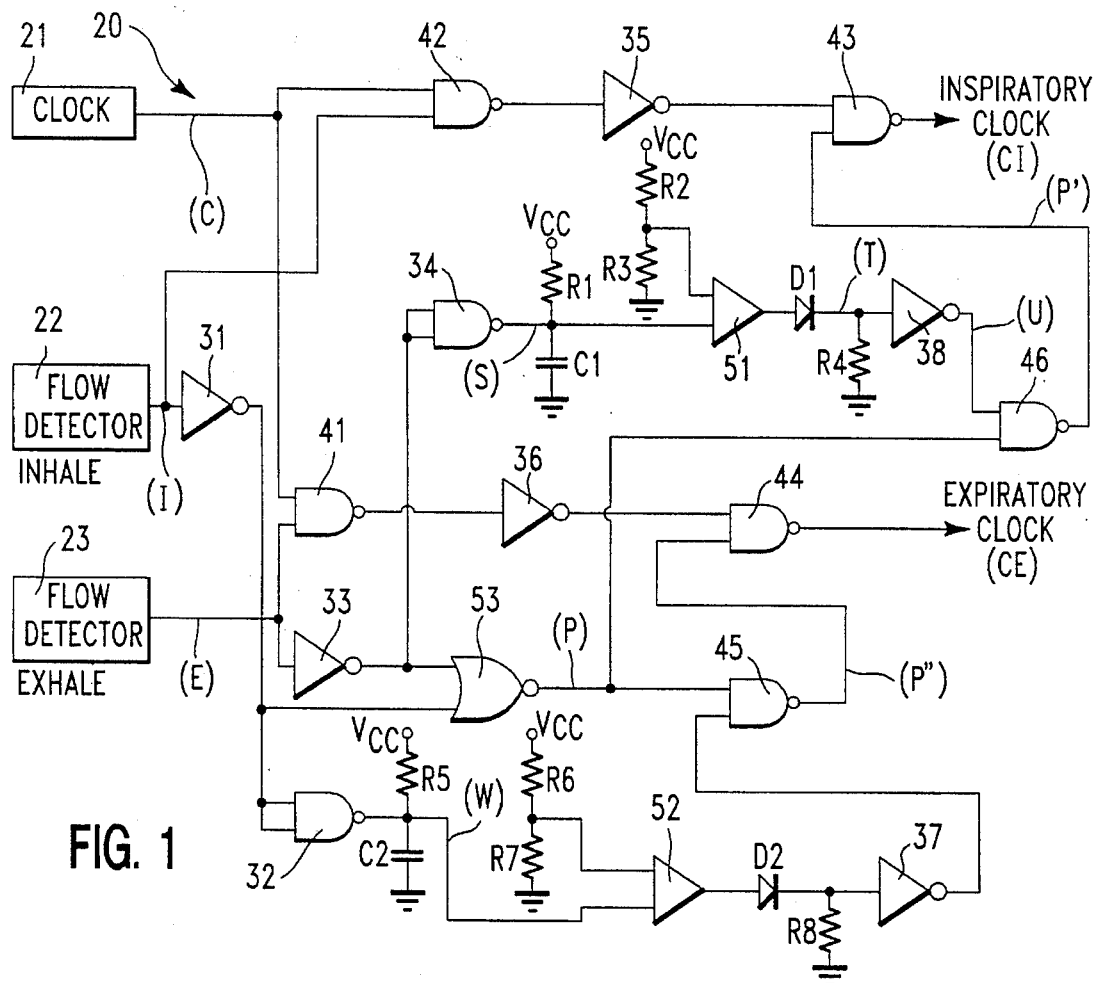
FIG. 1 is a logic diagram showing the preferred embodiment of the respiratory test circuit of the present invention.

Referring now to the drawings, FIG. 1 shows respiratory test circuit 20, having clock 21, and conventional inspiratory and expiratory flow detectors 22 and 23, respectively. Clock 21, which outputs timing pulses as clock signal (C), may be a conventional oscillator having a square-wave output, such as that shown in FIGS. 2 and 3. Inspiratory flow detector 22 outputs inspiratory signal (I) while expiratory flow detector 23 outputs expiratory signal (E). Circuit 20 produces output signals called inspiratory clock (CI) and expiratory clock (CE).

Commercially available flow transducers, such as those found in the KL Engineering Kozak Turbine Compensator KTC-3-D, mentioned above, may be used to implement flow detectors 22 and 23. According to conventional practice, detectors 22 and 23 may act as a flow and volummetric interface to measure both the volume of air expired by a subject and the numbers of breaths a subject takes per minute. Specifically, when used to test respirators, flow detector 22 mounts on the inspiratory side and flow detector 23 mounts on the expiratory side of the respirator (not shown).

Figure 2:
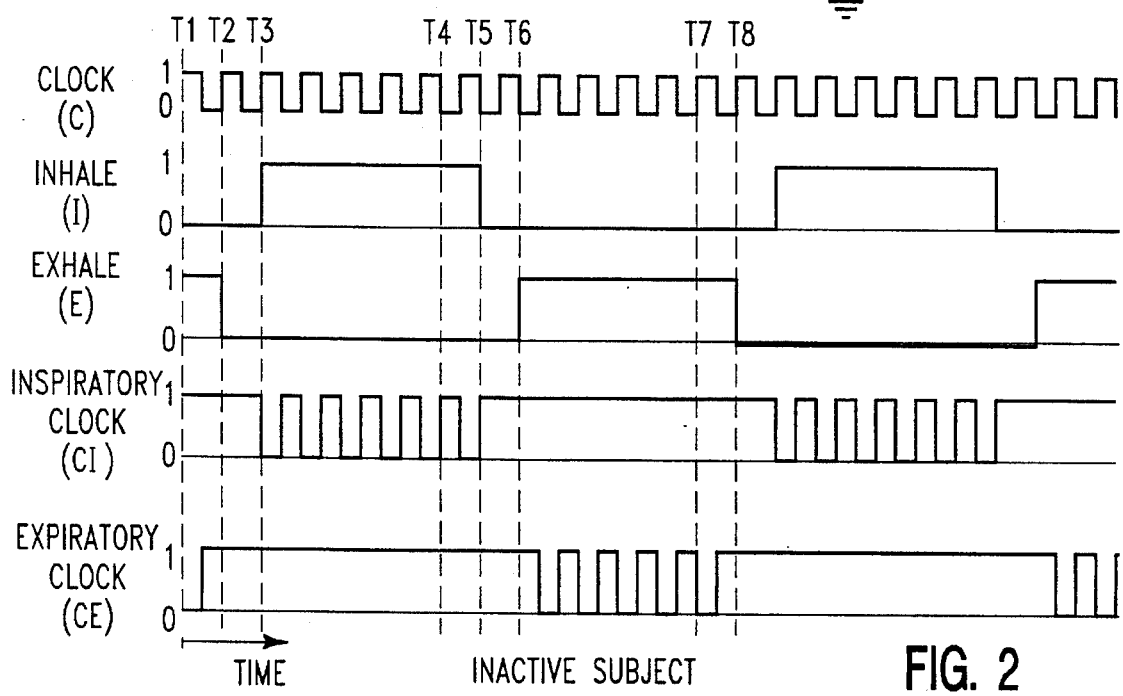
FIG. 2 is a time chart, illustrating waveforms at various points of the FIG. 1 respiratory test circuit when it is used to measure respiratory characteristics of an inactive subject.
Figure 3:
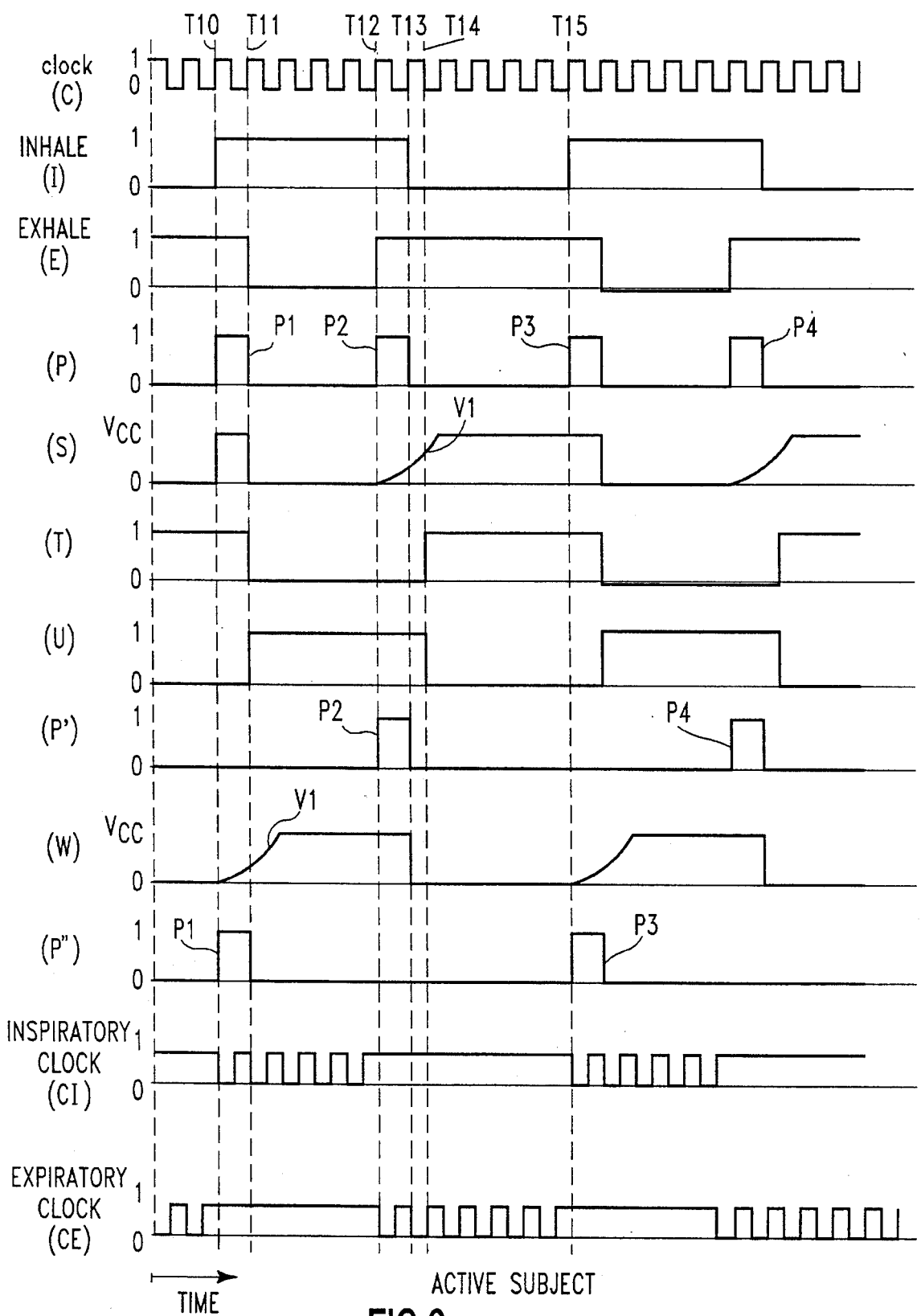
FIG. 3 is a time chart similar to that shown in FIG. 2 but illustrating waveforms produced by an active subject.

Square-wave clock signal (C), inspiratory signal (I), and expiratory signal (E) of FIGS. 2 and 3 are similar to those found in a conventional pneumotachograph. Logic 1 in inspiratory signal (I) represents that the subject is inhaling and logic 0 represents that the subject is not inhaling. Similarly, logic 1 in expiratory signal (E) represents that the subject is exhaling and logic 0 represents that the subject is not exhaling.

FIG. 2 illustrates the signals produced by a typical inactive subject. During period T3-TS, signal (I) equals logic 1 showing that the subject is inhaling. During period T6-T8, signal (E) equals logic 1 showing that the subject is exhaling. Also, during periods T2-T3 and TS-T6, signals (I) and (E) both equal logic 0 showing that the subject is neither inhaling nor exhaling. This correlation between the signals and the subject's breathing is generally accurate. In practice, however, a short period, equal to a clock cycle or two, normally exists near the trailing end of each inspiratory and expiratory pulse to allow detectors 22 and 23 to time out. As such, during these short timing-out periods, the signals (I) and (E) will improperly suggest that the subject is inhaling or exhaling.

For the FIG. 2 example, period T4-T5 represents a timing-out period for flow detector 22, and period T7-T8 represents a timing-out period for flow detector 23. Using this example, it is more accurate to say that the subject starts inhaling at time T3 and stops inhaling at some unknown time T4, after which inspiratory signal (I) remains at logic 1 until detector 22 times out at time T5. Similarly, the subject starts exhaling at time T6 and stops exhaling at some unknown time T7, after which expiratory signal (E) remains at logic 1 until detector 23 times out at time T8.

The existence of these short timing-out periods does not normally introduce an appreciable error when measuring breathing rates and volume of expired air for most subjects, and duration periods for inactive subjects. Usually, those that analyze the test results can adjust the results to account for the small timing-out errors. However, timing-out periods can introduce significant errors in the results of breath duration measurements for active subjects. For instance, the results of many tests improperly show that the sum of the durations for the individual inspiratory and expiratory periods exceeds the total test period. FIG. 3 illustrates this problem more clearly.

FIG. 3 shows inspiratory signal (I) and expiratory signal (E) for an active subject, such as a person jogging on a treadmill. In this situation, the subject starts to inhale at time T10, which occurs before detector 23 times out at time T11. Consequently, inspiratory signal (I) and expiratory signal (E) both equal logic 1 during period T10-T11. Likewise, the subject begins to exhale at time T12, which occurs before detector 22 times out at time T13. While it is not always clear from inspiratory signal (I) and expiratory signal (E) the precise time that the subject stopped inhaling or exhaling, it is clear that the subject stopped exhaling before beginning to inhale at time T10 and stopped inhaling before beginning to exhale at time T12. Also, it is generally true that as a subject exercises more actively, the actual periods between inhaling and exhaling approaches zero, i.e., there are no periods when the subject is neither inhaling nor exhaling. The timing logic of the present invention avoids the ambiguities in duration measurements, which the timing-out periods introduce, by using inspiratory signal (I) to help generate expiratory clock (CE), and vice versa.

Respiratory test circuit 20 includes logical inverters 31–38, NAND gates 41–46, operational amplifiers 51 and 52, and NOR gate 53. The output of detector 22 feeds an input of NOR gate 53 via inverter 31. The output of detector 23 feeds the other input of NOR gate 53 via inverter 33. NOR gate 53 outputs overlap signal (P), which comprises overlap pulses (P1)-(P4) that equal logic 1 during those overlap periods when inspiratory signal (I) and expiratory signal (E) both equal logic 1. Overlap signal (P) equals logic 0 at all other times. Signal (P) comprises overlap pulses (P1)-(P4).

For a highly active subject, such as that represented by the waveforms of FIG. 3, signal (P) equals logic 1 during the timing-out periods of detectors 22 and 23. For an inactive subject, such as that represented by the waveforms of FIG. 2, signal (P) always equals logic 0, because no time overlaps occur between signals (I) and (E). As described below in detail, circuit 20 uses signal (P) to resolve output ambiguities only when time-overlap pulses (P1)-(P4) appear in signal (P).

Clock signal (C) feeds timing pulses to one input of each of NAND gates 41 and 42. The output of detector 22 connects directly to the other input of NAND gate 42. The output of detector 23 connects directly to the other input of NAND gate 41. Inspiratory signal (I) gates clock signal (C) onto one input of NAND gate 43 via NAND gate 42 and inverter 35. Similarly, expiratory signal (E) gates clock signal (C) onto one input of NAND gate 44 via NAND gate 41 and inverter 36. Consequently, one input of each of NAND gates 43 and 44 equals clock signal (C) during those periods when signals (I) and (E) equal logic 1, respectively. These inputs of NAND gates 43 and 44 equal logic 0 at all other times. The other inputs to NAND gates 43 and 44 switch these gates on and off so that selected portions of the outputs of inverters 35 and 36 produce inspiratory clock (CI) and expiratory clock (CE), respectively.

As mentioned above, when no time overlaps between signals (I) and (E) occur, signal (P) equals logic 0. Under these circumstances, signal (P) will hold each of respective output signals (P') and (P") of NAND gates 45 and 46 at logic 1, which turns on NAND gates 43 and 44. NAND gate 43 inverts the output of inverter 35 to produce inspiratory clock (CI) at its output. Similarly, NAND gate 44 inverts the output of inverter 36 to produce expiratory clock (CE). Consequently, as shown in FIG. 2, inspiratory clock (CI)

equals logic 1 when inspiratory signal (I) equals logic 0, and equals an inverted version of clock signal (C) at all other times. Similarly, FIG. 2 shows expiratory clock (CE) equal to logic 1 when expiratory signal (E) equals logic 0, and equal to an inverted version of clock signal (C) at all other times. Since no time overlaps occur in this example, no ambiguities exist in inspiratory clock (CI) and expiratory clock (CE).

However, because time overlaps do occur when testing an active subject, ambiguities will exist that must be eliminated. Circuit 20 uses signals (I), (E), and (P) to remove these ambiguities. As mentioned above, circuit 20 causes signal (P) to equal logic 1 only during overlap periods. The first and third overlap pulses (P1) and (P3), respectively, occur during those periods when detector 23 times out. The second and fourth overlap pulses (P2) and (P4), respectively, occur during those periods when detector 22 times out. Circuit 20 employs the outputs of R-C timing circuits to remove pulses (P1) and (P3) from signal (P) via NAND gate 46 to produce signal (P'), and to remove pulses (P2) and (P4) from signal (P) via NAND gate 45 to produce signal (P").

A first R-C timing circuit comprises open-collector NAND gate 34, resistor R1 and capacitor C1. The inputs of NAND gate 34 connect in common to the output of inverter 33. One side of resistor R1 connects to DC supply voltage Vcc, while its other side connects to one side of capacitor C1 and the output of NAND gate 34. The other side of capacitor C1 connects to ground. For purposes of this description, voltage Vcc is considered to be greater than the voltage of logic 1. A voltage divider, made up of resistors R2 and R3 and designated herein as divider R2-R3, connects between voltage Vcc and ground. Operational amplifier 51 has two inputs, one connected to voltage divider R2-R3, and the other connected to the output of NAND gate 34. The output of operational amplifier 51 connects to one side of diode D1. The other side of diode D1 connects to grounded resistor R4 and the input of inverter 38. The output of inverter 38 connects to one input of NAND gate 46.

A second R-C timing circuit, which is similar in structure and function to the first R-C timing circuit, comprises open-collector NAND gate 32, resistor R5 and capacitor C2. The inputs to NAND gate 32 connect to the output of inverter 31. One side of resistor R5 connects to DC supply voltage Vcc, while its other side connects to one side of capacitor C2 and the output of NAND gate 32. The other side of capacitor C2 connects to ground. A voltage divider R6-R7, which contains resistors R6 and R7, connects between voltage Vcc and ground. Operational amplifier 52 has two inputs, one connected to voltage divider R6-R7, and the other connected to the output of NAND gate 32. The output of operational amplifier 52 connects to one side of diode D2. The other side of diode D2 connects to grounded resistor R8 and the input of inverter 37. The output of inverter 37 connects to one input of NAND gate 45.

NAND gates 32 and 34, which act as inverters, allow capacitors C1 and C2 to slowly charge through their respective resistors R1 and R5. More specifically, an inverted version of expiratory signal (E) inputs NAND gate 34. The waveform (S) represents the output of NAND gate 34. When the subject exhales, NAND gate 34 has an input equal to logic 0 and an output equal to logic 1, which just floats because the collector being open is not connected directly to voltage Vcc. However, because resistor R1 connects directly to voltage Vcc, capacitor C1 charges slowly through resistor R1 as depicted in waveform (S) of FIG. 3 starting at time T12. When the charge on capacitor C1 has reached set point voltage V1 of the voltage divider R2-R3, the output of operational amplifier 51 changes state from a relatively low voltage to voltage Vcc. In the waveform (S) of FIG. 3, capacitor C1 reaches the set point voltage value V1 at time T14, which is set to be just beyond time T13, the time when inspiratory signal (I) times out and falls to logic 0.

Waveform (T) of FIG. 3 represents the output of operational amplifier 51. Inverter 38 inverts waveform (T) into waveform (U) and applies it to the input of NAND gate 46. When waveform (U) equals logic 1, NAND gate 46 turns on and transmits waveform (P'), which consists of selected overlap pulses of signal (P), to NAND gate 43.

In the other state when the subject inhales and expiratory signal (E) equals logic 0, the output of NAND gate 34 equals logic 0. This quickly discharges capacitor C1 (e.g., see time T11 in FIG. 3), and puts the output of operational amplifier 52 in its low-voltage state. Diode D1 enables resistor R4 to pull the input of inverter 38 to logic 0 causing its output signal (U) to equal logic 1. Output signal (U) remains equal to logic 1 until capacitor C1 becomes charged again, i.e., after the subject has stopped inhaling, and detector 22 has timed out plus a short time equal to period T13-T14. With signal (U) equal to logic 1, any pulses in signal (P), such as pulse (P2), reaching the input of NAND gate 46 will pass as signal (P') to shut off NAND gate 43, thereby blocking the ambiguous overlaps. For the first inspiratory cycle in the FIG. 3 example, signal (P') permits clock pulses in inspiratory clock (CI) to pass NAND gate 43 during the period T10-T12, but blocks clock pulses during the timing-out period T12-T13.

The second R-C timing circuit operates in like manner such that output signal (P") comprises pulses (P1) and (P3). Waveform (W), which is similar to waveform (S), represents the charge on capacitor C2. For the expiratory cycle starting at time T12 in FIG. 3, overlap signal (P") equals logic 0 and, therefore, permits clock pulses to pass NAND gate 43 for the period T12-T15. However, overlap pulse (P3) in signal (P") blocks clock pulses from passing NAND gate 43, removing overlapping pulses and preventing ambiguities to exist between inspiratory clock (CI) and expiratory clock (CE). Inspiratory clock (CI) and expiratory clock (CE) may now be measured in a conventional manner (e.g., by counting the timing pulses) to ascertain the volume of expired air, the flow rates, and the inspiratory and expiratory durations. Of course, because ambiguities were removed from inspiratory clock (CI) and expiratory clock (CE), the sum of the individual inspiratory and expiratory durations will not exceed the total test duration.

Although a preferred embodiment of the present invention has been shown and described in detail herein, many other varied embodiments that incorporate the teachings of the present invention may be easily constructed by those skilled in the art. It is therefore to be understood, that the foregoing disclosure and drawings are merely illustrative of the principles of this invention and are not to be interpreted in a limiting sense. It is to be understood that the invention should not be limited to the exact details of construction shown and described because obvious modifications will occur to a person skilled in the art.

What is claimed is:

1. A respiratory test circuit comprising:

a clock input means for receiving clock pulses;

an inhalation input means for receiving a two-state inhalation signal having first and second inhalation states, said inhalation signal being at said first inhalation state during an inhalation period plus an inhalation timing-out period, and being at said second inhalation state at all other times;

an exhalation input means for receiving a two-state exhalation signal having first and second exhalation states, said exhalation signal being at said first exhalation state during an exhalation period plus an exhalation timing-out period, and being at said second exhalation state at all other times;

a logic means having an inspiratory clock output and an expiratory clock output, said logic means connected to said clock input means, said inhalation input means, and said exhalation input means for transmitting said clock pulses from said clock input means to said inspiratory clock output when said inhalation signal is at said first inhalation state and to said expiratory clock output when said exhalation signal is at said first exhalation state; and said logic means including overlap detection means for generating an overlap pulse when said inhalation signal is at said first inhalation state and said exhalation signal simultaneously is at said first exhalation state, and gate means responsive to said overlap pulse for selectively controlling the transmission of said clock pulses to said inspiratory and expiratory clock outputs.

2. The circuit of claim 1 wherein said gate means responsive to said overlap pulse selectively blocks the transmission of said clock pulses to said inspiratory and expiratory clock outputs.

3. The circuit of claim 2 wherein said overlap detection means generates a first set of said overlap pulses when said inhalation signal is at said first state during said timing-out period of said exhalation signal, and generates a second set of said overlap pulses when said exhalation signal is at said first state during said timing-out period of said inhalation signal.

4. The circuit of claim 3 wherein said gate means includes means for blocking the transmission of said clock pulses to said inspiratory clock output in response to said second set of said overlap pulses, and for blocking the transmission of said clock pulses to said expiratory clock output in response to said first set of said overlap pulses.

5. The circuit of claim 4 wherein said overlap detection means includes a first timing means for detecting a change in said inhalation signal from said second inhalation state to said first inhalation state for generating said first set of said overlap pulses, and a second timing means for detecting a change in said exhalation signal from said second exhalation state to said first exhalation state for generating said second set of said overlap pulses.

6. The circuit of claim 5 wherein each said timing means includes a time circuit having a time constant greater than said timing-out periods.

7. The circuit of claim 6 wherein each said time circuit includes a resistor-capacitor time circuit 8. A respiratory test circuit comprising:

a clock means for providing clock pulses;

an inhalation flow detector means for detecting the presence of an inspiratory flow and providing a two-state inhalation signal having first and second inhalation states, said inhalation signal being at said first inhalation state during the duration of said inspiratory flow plus an inhalation timing-out period, and being at said second inhalation state at all other times;

an exhalation flow detector means for detecting the presence of an expiratory flow and providing a two-state exhalation signal having first and second exhalation states, said exhalation signal being at said first exhalation state during the duration of said expiratory flow plus an exhalation timing-out period, and being at said second exhalation state at all other times;

a logic means having an inspiratory clock output and an expiratory clock output, said logic means connected to said clock means and said inhalation and exhalation flow detector means for transmitting said clock pulses from said clock means to said inspiratory clock output when said inhalation signal is at said first inhalation state and to said expiratory clock output when said exhalation signal is at said first exhalation state; and said logic means including overlap detection means for generating an overlap pulse when said inhalation signal is at said first inhalation state and said exhalation signal simultaneously is at said first exhalation state, and gate means responsive to said overlap pulse for selectively controlling the transmission of said clock pulses to said inspiratory and expiratory clock outputs.

9. The circuit of claim 8 wherein said gate means responsive to said overlap pulse selectively blocks the transmission of said clock pulses to said inspiratory and expiratory clock outputs.

10. The circuit of claim 9 wherein said overlap detection means generates a first set of said overlap pulses when said inhalation signal is at said first state during said timing-out period of said exhalation signal, and generates a second set of said overlap pulses when said exhalation signal is at said first state during said timing-out period of said inhalation signal.

11. The circuit of claim 10 wherein said gate means includes means for blocking the transmission of said clock pulses to said inspiratory clock output in response to said second set of said overlap pulses, and for blocking the transmission of said clock pulses to said expiratory clock output in response to said first set of said overlap pulses.

12. The circuit of claim 11 wherein said overlap detection means includes a first timing means for detecting a change in said inhalation signal from said second inhalation state to said first inhalation state for generating said first set of said overlap pulses, and a second timing means for detecting a change in said exhalation signal from said second exhalation state to said first exhalation state for generating said second set of said overlap pulses.

13. The circuit of claim 12 wherein each said timing means includes a time circuit having a time constant greater than said timing-out periods.

14. The circuit of claim 13 wherein each said time circuit includes a resistor-capacitor time circuit 15. The circuit of claim 14 wherein said first timing means has an open-collector NAND gate having inputs connected in common to said inhalation flow detector means and an output connected to one of said time circuits, and said second timing means has an open-collector NAND gate having inputs connected in common to said exhalation flow detector means and an output connected to another of said time circuits.

16. A respiratory testing method comprising:

generating a set of clock pulses;

detecting the presence of an inspiratory flow and generating a two-state inhalation signal having first and second inhalation states, said inhalation signal being at said first inhalation state during the duration of said inspiratory flow plus an inhalation timing-out period, and being at said second inhalation state at all other times;

detecting the presence of an expiratory flow and generating a two-state exhalation signal having first and second exhalation states, said exhalation signal being at said first exhalation state during the duration of said expiratory flow plus an exhalation timing-out period, and being at said second exhalation state at all other times;

transmitting said clock pulses to form an inspiratory clock output when said inhalation signal is at said first inhalation state;

transmitting said clock pulses to form an expiratory clock output when said exhalation signal is at said first exhalation state; and generating an overlap pulse when said inhalation signal is at said first inhalation state and said exhalation signal simultaneously is at said first exhalation stake, and selectively controlling the transmission of said clock pulses to said inspiratory and expiratory clock outputs in response to said overlap pulse.

17. The method of claim 16 wherein the selectively controlling of the transmission of said clock pulses to said inspiratory and expiratory clock outputs in response to said overlap pulse is a selective blocking of the transmission of said clock pulses.

18. The method of claim 17 further including generating a first set of said overlap pulses when said inhalation signal is at said first state during said timing-out period of said exhalation signal, and generating a second set of said overlap pulses when said exhalation signal is at said first state during said timing-out period of said inhalation signal.

19. The method of claim 18 further including blocking the transmission of said clock pulses to said inspiratory clock output in response to said second set of said overlap pulses, and blocking the transmission of said clock pulses to said expiratory clock output in response to said first set of said overlap pulses.

20. The method of claim 19 further including generating said first set of said overlap pulses when said inhalation signal changes from said second inhalation state to said first inhalation state, and generating said second set of said overlap pulses when said exhalation signal changes from said second exhalation state to said first exhalation state.

* * * * *